United States Patent [19]
Boyd et al.

[11] Patent Number: 6,136,813
[45] Date of Patent: Oct. 24, 2000

[54] PHARMACEUTICAL TREATMENT

[75] Inventors: Malcolm Richard Boyd; David Sutton, both of Epsom, United Kingdom

[73] Assignee: Beecham plc, Brentford, United Kingdom

[21] Appl. No.: 08/287,476

[22] Filed: Aug. 8, 1994

Related U.S. Application Data

[63] Continuation of application No. 08/010,635, Jan. 28, 1993, abandoned, which is a continuation of application No. 07/807,706, Dec. 16, 1991, abandoned, which is a continuation of application No. 07/487,190, Mar. 1, 1990, abandoned.

[30] Foreign Application Priority Data

Mar. 3, 1989 [GB] United Kingdom .................. 8904855

[51] Int. Cl.7 .................................................... A61K 31/52
[52] U.S. Cl. .......................... 514/262; 514/261; 514/264
[58] Field of Search ................................... 514/261, 262, 514/264

[56] References Cited

U.S. PATENT DOCUMENTS

| | | | |
|---|---|---|---|
| 4,199,574 | 4/1980 | Schaeffer | 424/200 |
| 4,230,708 | 10/1980 | De Clercq et al. | 424/253 |
| 4,556,659 | 12/1985 | Verheyden et al. | 514/262 |
| 4,649,140 | 3/1987 | Schaeffer | 514/261 |
| 4,942,166 | 7/1990 | Harnden et al. | 514/262 |
| 5,059,604 | 10/1991 | Krenitsky et al. | 514/261 |
| 5,075,445 | 12/1991 | Jarvest et al. | 544/276 |

FOREIGN PATENT DOCUMENTS

| | | | |
|---|---|---|---|
| 0 216 459 | 7/1986 | European Pat. Off. | C07D 473/18 |

OTHER PUBLICATIONS

Alexander et al., "Natural History and Therapy of Chronic Hepatitis B Virus Infection", *The American Journal of Medicine*, 85(2A), pp. 143–146 (1988).

Boyd et al., Antimicrobial Agents and Chemotherapy, 31(8), pp. 1238–2342 (1987).

Vere Hodge et al., Antimicrobial Agents and Chemotherapy, 31(8), pp. 223–229 (1989).

Alexander et al., British Medical Journal, 292(6525), pp. 915–916 (1986).

Thomas et al., British Medical Journal, 41(4), pp. 374–380 (1985).

Korba et al., Antimicrobial Agents and Chemotherapy, 40(5), pp. 1282–1284.

Beacham Group PLC CA:103 1235099, 1985.

Tippie et al CA:102, 214686 b, 1985.

Johansson et al CA: 104: 50735e, 1986.

*Primary Examiner*—Russell Travers
*Attorney, Agent, or Firm*—Dara L. Dinner; Stephen Venetianer; Charles M. Kinzig

[57] ABSTRACT

Pharmaceutical use of a compound of formula (A):

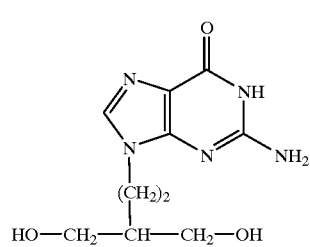

(A)

or a pro-drug, or a pharmaceutically acceptable salt, phosphate ester and/or acyl derivative of either of the foregoing; in the treatment of hepatitis B virus infections.

9 Claims, No Drawings

PHARMACEUTICAL TREATMENT

This application is a continuation of application Ser. No. 08/10,635, filed Jan. 28, 1993, now abandoned, which is a continuation of application Ser. No. 07/807,706, filed Dec. 16, 1991, now abandoned, which is a continuation of application Ser. No. 07/487,190, filed Mar. 1, 1990, now abandoned.

This invention relates to a method of treatment of viral infections caused by hepatitis B virus, in humans and animals, and to the use of compounds in the preparation of a medicament for use in the treatment of such infections.

EP-A-141927 (Beecham Group p.l.c.; corresponding to U.S. Pat. No. 5,075,445) discloses penciclovir, the compound of formula (A):

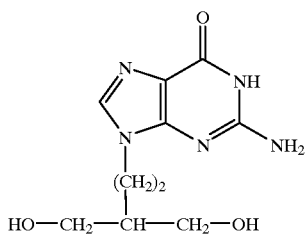

(A)

and salts, phosphate esters and acyl derivatives thereof, as antiviral agents. The sodium salt hydrate of penciclovir is disclosed in EP-A-216459 (Beecham Group p.l.c.; corresponding to U.S. Pat. No. 5,246,937).

Pro-drugs of the compound of formula (A) are of formula (B):

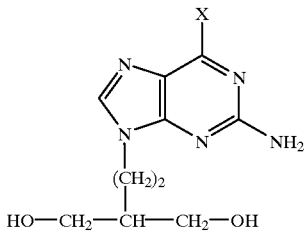

(B)

and salts and derivatives thereof as defined under formula (A); wherein X is $C_{1-6}$ alkoxy, $NH_2$ or hydrogen. The compounds of formula (B) wherein X is $C_{1-6}$ alkoxy or $NH_2$ are disclosed in EP-A-141927 and the compound of formula (B) wherein X is hydrogen, disclosed in EP-A-182024 (Beecham Group p.l.c.). A particularly preferred example of a compound of formula (B) is that wherein X is hydrogen and wherein the two OH groups are in the form of the acetyl derivative, described in Example 2 of EP-A-182024, hereinafter referred to as famciclovir.

The compounds of formulae (A) and (B) and salts and derivatives thereof have been described as useful in the treatment of infections caused by herpesviruses, such as herpes simplex type 1, herpes simplex type 2 and varicella zoster viruses.

It has now been discovered that these compounds have activity against the hepatitis B virus, and are therefore of potential use in the treatment of hepatitis B virus infections.

Accordingly, the present invention provides a method of treatment of hepatitis B virus infections in mammals, including humans, which method comprises the administration to the mammal in need of such treatment, an effective amount of a compound of formula (A):

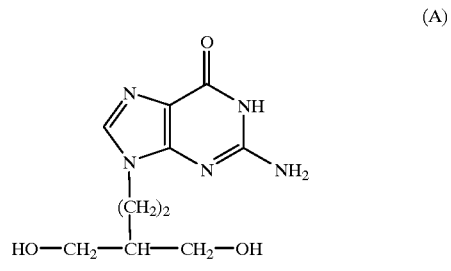

(A)

or a pro-drug, or a pharmaceutically acceptable salt, phosphate ester and/or acyl derivative of either of the foregoing.

The term 'acyl derivative' is used herein to include any derivative of the compounds of formula (A) in which one or more acyl groups are present. Such derivatives are included as pro-drugs of the compounds of formula (A) in addition to those derivatives which are Der se biologically active.

Examples of pro-drugs, pharmaceutically acceptable salts and derivatives are as described in the aforementioned European Patent references, the subject matter of which are incorporated herein by reference.

A particular pro-drug of interest is 9-(4-acetoxy-3-acetoxymethylbut-1-yl)-2-aminopurine, known as famciclovir.

The compound of formula (A) may also be in one of the forms disclosed in EP-A-216459 (Beecham Group p.l.c.).

The compound of formula (A), pro-drugs, salts and derivatives may be prepared as described in the aforementioned European Patent references.

The compound may be administered by the oral route to humans and may be compounded in the form of syrup, tablets or capsule. When in the form of a tablet, any pharmaceutical carrier suitable for formulating such solid compositions may be used, for example magnesium stearate, starch, lactose, glucose, rice, flour and chalk. The compound may also be in the form of an ingestible capsule, for example of gelatin, to contain the compound, or in the form of a syrup, a solution or a suspension. Suitable liquid pharmaceutical carriers include ethyl alcohol, glycerine, saline and water to which flavouring or colouring agents may be added to form syrups.

For parenteral administration, fluid unit dose forms are prepared containing the compound and a sterile vehicle. The compound depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the compound of the invention.

Preferred parenteral formulations include aqueous formulations using sterile water or normal saline, at a pH of 7.4, and above.

As is common practice, the compositions will usually be accompanied by written or printed directions for use in the medical treatment concerned.

An amount effective to treat a hepatitis B virus infection depends on the nature and severity of the infection and the weight of the mammal.

A suitable dosage unit might contain from 50 mg to 1 g of active ingredient, for example 100 to 500 mg. Such doses may be administered 1 to 4 times a day or more usually 2 or 3 times a day. The effective dose of compound will, in general, be in the range of from 0.2 to 40 mg per kilogram of body weight per day or, more usually, 10 to 20 mg/kg per day.

The present invention also provides the use of a compound of formula (A) or a pro-drug, or a pharmaceutically acceptable salt, phosphate ester and/or acyl derivative of either of the foregoing, in the preparation of a medicament for use in the treatment of hepatitis B virus infections in mammals, including humans. Such treatment may be carried out in the manner as hereinbefore described.

The present invention further provides a pharmaceutical composition for use in the treatment of hepatitis B virus infections, which comprises an effective amount of a compound of formula (A) or a pro-drug, or a pharmaceutically acceptable salt, phosphate ester and/or acyl derivative of either of the foregoing, and a pharmaceutically acceptable carrier. Such compositions may be prepared in the manner as hereinafter described.

The activity of the compounds of formula (A) and pro-drugs, salts, phosphate ester and/or acyl derivatives against hepatitis B virus, may be identified according to the following Test Protocol.

Test for Activity against Hepatitis B virus in ducks

Penciclovir and famciclovir were each tested at two dose levels against hepatitis B virus in ducks. Administration was by oral gavage to two ducks at each dose level.

Dosage was twice daily Monday to Friday inclusive; once daily Saturday and Sunday, continuing for 3 weeks.

The compounds showed activity against duck hepatitis B virus in the above test. Activity was demonstrated by a large reduction in the plasma concentration of duck hepatitis virus DNA and DNA polymerase during treatment. The Table shows the blood levels of administered drug.

TABLE

Blood levels of penciclovir in Pekin ducks after oral dosing with penciclovir or famciclovir

| Compound administered | Dose (mg/kg) | Duck No. | Penciclovir concentration ($\mu$M) in blood at (min) | | | | | | AUC[5] ($\mu$M hr) |
|---|---|---|---|---|---|---|---|---|---|
| | | | 15 | 30 | 60 | 120 | 240 | 360 | |
| penciclovir[1] | 100 | 142 | 43 | 44 | 40 | 18 | 3.6 | 1.1 | 92 |
| | | 163 | 42 | 38 | 44[3] | 21 | 2.7 | ~0.5 | 95 |
| | 20 | 139 | 24 | 28 | 18[3] | 12 | 2.8 | ~0.5 | 55 |
| | | 169 | 41 | 30 | 19[3] | 10 | 2.6 | N.D.[4] | 57 |
| famciclovir[1] | 25 | 111 | 22 | 31 | 34 | 33 | 14 | 6.1 | 126 |
| | | 153 | 18 | 20[2] | 25 | 20 | 4.4 | ~0.5 | 90 |
| | 5 | 117 | 8.7 | 8.4[2] | 7.5 | 2.0 | ~0.5 | N.D.[4] | 15 |
| | | 154 | 5.1 | 3.9[2] | 3.5 | 2.0 | 1.4 | 1.0 | 12 |

Notes
[1]Penciclovir administered as a suspension in 1% carboxymethyl cellulose in water containing 1% tween 80. Famciclovir administered as a solution in water.
[2]Samples collected at 32 min.
[3]Samples collected at 65 min.
[4]N.S. = not detected; limit of assay 0.5 $\mu$M.
[5]AUC = Area under the 0–6 hr. concentration/time curve.

What is claimed is:

1. A method of treatment of hepatitis B virus infections in mammals which method comprises the administration to the mammal in need of such treatment, an effective amount of a compound of formula (A):

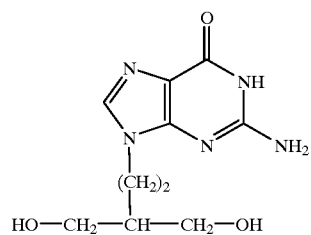

(A)

or a pro-drug, or a pharmaceutically acceptable salt, phosphate ester and/or acyl derivative of either of the foregoing.

2. A method according to claim 1 wherein the compound administered is penciclovir, or a pharmaceutically acceptable salt of formula (A).

3. A method according to claim 1 wherein the compound administered is the sodium salt hydrate of the compound of formula (A).

4. A method according to claim 3 wherein the compound is administered parenterally in an aqueous formulation.

5. A method according to claim 1 wherein the compound administered is in a 50 mg to 1 g unit dose.

6. A method of treatment of hepatitis B virus infections in mammals which method comprises the administration to said mammal in need of such treatment, an effective amount of a compound of formula (B):

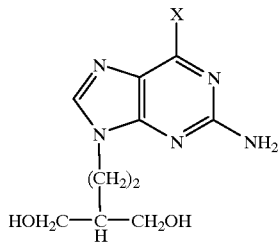
(B)

wherein X is $C_{1-6}$ alkoxy, $NH_2$, or hydrogen; and a pharmaceutically acceptable salt, phosphate ester, or acyl derivative derivative thereof.

7. A method according to claim 6 wherein the compound is 9-(4-acetoxy-3-acetoxymethylbut-1-yl)-2-aminopurine.

8. A method according to claim 6 wherein the compound administered is in a 50 mg to 1 g unit dose.

9. A method according to claim 6 wherein the compound is administered orally.

* * * * *